US006740636B2

United States Patent
Horuk

(10) Patent No.: US 6,740,636 B2
(45) Date of Patent: May 25, 2004

(54) NON-PEPTIDE CCR1 RECEPTOR ANTAGONISTS IN COMBINATION WITH CYCLOSPORIN A FOR THE TREATMENT OF HEART TRANSPLANT REJECTION

(75) Inventor: Richard Horuk, Lafayette, CA (US)

(73) Assignee: Schering Aktiengesellschaft, Berlin (DE)

(*) Notice: Subject to any disclaimer, the term of this patent is extended or adjusted under 35 U.S.C. 154(b) by 270 days.

(21) Appl. No.: 09/915,411

(22) Filed: Jul. 25, 2001

(65) Prior Publication Data

US 2002/0039997 A1 Apr. 4, 2002

Related U.S. Application Data

(60) Provisional application No. 60/231,282, filed on Sep. 8, 2000, and provisional application No. 60/222,053, filed on Jul. 31, 2000.

(51) Int. Cl.$^7$ ............................................... A61K 38/00
(52) U.S. Cl. ................... 514/9; 514/255.01; 514/235.8; 514/254.08; 544/121; 544/231; 544/391
(58) Field of Search ................................ 514/9, 252.12

(56) References Cited

U.S. PATENT DOCUMENTS

6,207,665 B1    3/2001    Bauman et al.

FOREIGN PATENT DOCUMENTS

| WO | WO 98/38167 | 9/1998 |
|---|---|---|
| WO | WO 99/37617 | 7/1999 |
| WO | WO 99/37619 | 7/1999 |
| WO | WO 99/37651 | 7/1999 |
| WO | WO 99/40061 | 8/1999 |
| WO | WO00/16796 | 3/2000 |
| WO | WO00/44365 | 3/2000 |

OTHER PUBLICATIONS

Horuk, et al., "A Non–peptide Functional Antagonist of the CCR1 Chemokine Receptor Is Effective in Rat Heart Transplant Rejection", *J. Biol. Chem.*, (2001) 276(6):4199–4204.
Gröne et al., "Met–RANTES reduces vascular and tubular damage during acute renal transplant rejection: blocking monocyte arrest and recruitment", *FASEB J.*, (1999) 13:1371:1383.
Liang et al., "Species selectivity of a small molecule antagonist for the CCR1 chemokine receptor", *Eur. J. Phar.*, (2000) 389:41–49.
Liang et al., "Identification and Characterization of a Potent, Selective, and Orally Active Antagonist of the CC Chemokine Receptor–1", *J. Biol. Chem.*, (2000) 275(25):19000–19008.
Hesselgesser et al., "Identification and Characterization of Small Molecule Functional antagonists of the CCR1 Chemokine Receptor", *J. Biol. Chem.*, (1998) 273(25):15687–15692.
Ng et al., "Discovery of Novel Non–Peptide CCR1 Receptor Antagonists", *J. Med. Chem.*, (1999) 42:4680–4694.
Gao et al., "Targeting of the chemokine receptor CCR1 suppresses development of acute and chronic cardiac allograft rejection", *J. Clin. Invest.*, (2000) 105(1):35–44.
Horuk et al., "CCR1 specific non–peptide antagonist efficacy in a rabbit allograft rejection model", *Immunol. Lett.* (2001) 76(3):193–201.

Primary Examiner—Karen Cochrane Carlson
Assistant Examiner—Anand U Desai
(74) Attorney, Agent, or Firm—Carol J. Roth

(57) ABSTRACT

This invention is directed to pharmaceutical compositions useful in treating heart transplant rejection in mammals comprising a pharmaceutically acceptable excipient, a therapeutically effective amount of a non-peptide CCR1 receptor antagonist and a sub-nephrotoxic amount of cyclosporin A.

17 Claims, 7 Drawing Sheets

FIGURE 5

| Group | N | n | Rejection Grade |
|---|---|---|---|
| Control-Oil | 2 | 9 | 1.72 ± 0.24 |
| Control-Cyclosporin A | 3 | 15 | 1.45 ± 0.25 |
| Compound-Oil | 2 | 9 | 1.44 ± 0.29 |
| Compound-Cyclosporin A | 3 | 12 | 0.65 ± 0.14 |

Cyclosporin A was administered at 2.5 mg/kg. A CCR1 antagonist of the invention was administered at 50 mg/kg. N = number of animals, n = number of tissue blocks examined per group. Mean ± SEM.

NON-PEPTIDE CCR1 RECEPTOR ANTAGONISTS IN COMBINATION WITH CYCLOSPORIN A FOR THE TREATMENT OF HEART TRANSPLANT REJECTION

This is a non-provisional application claiming priority under 35 U.S.C § 119 provisional application Nos. 60/222,053, filed Jul. 31, 2000, and 60/231,282, filed Sep. 8, 2000.

FIELD OF THE INVENTION

The present invention relates to pharmaceutical compositions useful in the treatment of heart transplant rejection in mammals which comprise a pharmaceutically acceptable excipient, a therapeutically effective amount of a non-peptide CCR1 receptor antagonist and a sub-nephrotoxic amount of cyclosporin A. The present invention also relates to a method of using such pharmaceutical compositions in treating heart transplant rejection in mammals.

BACKGROUND OF THE INVENTION

An important component of the inflammatory process involves the migration and activation of select populations of leukocytes from the circulation and their accumulation in the affected tissue. While the idea of leukocyte trafficking is not new, it has enjoyed a renaissance recently following the discovery and characterization of the selectin and integrin families of adhesion molecules and the large family of selective chemotactic cytokines known as chemokines. Chemokine receptors are expressed on leukocytes and process the signals following the binding of the chemokine whereby such signals are eventually transduced into migration or activation of the leukocytes towards the source of the chemokine. Therefore, by regulating the migration and activation of leukocytes from the peripheral blood to extravascular sites in organs, skin, articulations or connective, tissue, chemokines play a critical role in the maintenance of host defense as well as in the development of the immune response.

Originally, the chemokine family of molecules was divided into two groups: the "C—X—" subfamily and the "C—C" subfamily. The characteristic feature of both of these subfamilies is the presence of four cysteine residues in highly conserved positions in the molecules. In the "C—C" chemokine subfamily, the first two residues are adjacent to each other, while in the "C—X—C" subfamily, a single amino acid residue separates the cysteine residues. A recent description of a "—C—" chemokine appears to represent a new family of chemokines in that the "—C" chemokine lacks two of the four cysteine residues present in the "C—C" subfamily or the "C—X—C" subfamily.

One member of the "C—C" subfamily of chemokines is macrophage inflammatory protein-1α ("MIP-1α"). It is expressed by cells such as macrophages, T and B lymphocytes, neutrophils and fibroblasts. A recent study (see Karpus, W. J. et al., *J. Immunol.* (1995), Vol. 155, pp. 5003–5010) provides strong in vivo concept validation for a role of MIP-1α in a mouse experimental autoimmune encephalomyelitis ("EAE") model of multiple sclerosis. Multiple sclerosis is an autoimmune disease mediated by T and B lymphocytes and macrophages, resulting in extensive inflammation and demyelination of white matter in the central nervous system. The study showed that antibodies to MIP-1α prevented the development of both initial and relapsing disease as well as preventing the infiltration of mononuclear cells into the central nervous system. Treatment with the antibodies was also able to ameliorate the severity of ongoing clinical disease. These results led the investigators to conclude that MIP-1α plays an important role in the etiology of multiple sclerosis. Another study (see Godiska, R. et al., *J. Neuroimmunol.* (1995), Vol. 58, pp. 167–176) demonstrated the upregulation of mRNA for a number of chemokines, including MIP-1α, in the lesions and spinal cord of SJL mice (a strain of mice susceptible to $Th_1$ diseases such as EAE) during the course of acute EAE.

RANTES is another member of the C—C chemokine subfamily (the name RANTES is an acronym derived from some of the original observed and predicted characteristics of the protein and its gene: Regulated upon Activation Normal T cell Expressed presumed Secreted). A wide variety of tissues have been found to express RANTES in a similar pattern to MIP-1α. There is evidence from a number of studies to implicate the abnormal production of RANTES in the progression of rheumatoid arthritis (see Rathanaswami, P. et al., *J. Biol. Chem.* (1993), Vol. 268, pp. 5834–5839 and Snowden, N. et al., *Lancet* (1994), Vol. 343, pp. 547–548). Rheumatoid arthritis is a chronic inflammatory disease characterized in part by a memory T lymphocyte and monocyte infiltration, which is believed to be mediated by chemotactic factors released by inflamed tissues. There is strong evidence from other studies implicating RANTES in the pathophysiology of rheumatoid arthritis (see Barnes, D. A. et al, *J. Clin. Invest* (1998), Vol. 101, pp. 2910–2919 and Plater-Zyberk, C. A. et al., *Immunol. Lett.* (1997), Vol. 57, pp. 117–120). For example, in a rat adjuvant-induced arthritis ("AIA") model, antibodies to RANTES greatly reduced the development of disease.

These studies and others provide strong evidence that MIP-1α levels are increased in EAE models of multiple sclerosis and that RANTES levels are increased in rheumatoid arthritis (see, e.g., Glabinski, A. R. et al, *Am. J. Pathol.* (1997), Vol. 150, pp. 617–630; Glabinski, A. R. et al., *Methods Enzymol.* (1997), Vol. 288, pp. 182–190; and Miyagishi, R. S. et al., *J. Neuroimmunol.* (1997), Vol. 77, pp. 17–26). In addition, as described above, these chemokines are chemoattractants for T cells and monocytes, which are the major cell types that are involved in the pathophysiology of these diseases. Therefore, any molecule that inhibits the activity of either of these chemokines would be beneficial in treating these diseases and would therefore be useful as an anti-inflammatory agent.

There also exists strong evidence linking RANTES to organ transplant rejection. The infiltration of mononuclear cells into the interstitium of organ transplants is the hallmark of acute cellular rejection. This cellular infiltrate primarily consists of T cells, macrophages and eosinophils. In a study of RANTES expression during acute renal allograft rejection, RANTES mRNA expression was found in infiltrating mononuclear cells and renal tubular epithelial cells and RANTES itself was found to be bound to the endothelial surface of the microvasculature within the rejecting graft (see Pattison, J. et al., *Lancet* (1994), Vol. 343, pp. 209–211 and Wiedermann, C. J. et al., *Curr. Biol* (1993), Vol. 3, pp. 735–739). A recent study (see Pattison, J. M. et al, *J. Heart Lung Transplant.* (1996), Vol. 15, pp. 1194–1199) suggests that RANTES may play a role in graft atherosclerosis. Increased levels of RANTES, both mRNA and protein, were detected in mononuclear cells, myofibroblasts, and endothelial cells of arteries undergoing accelerated atherosclerosis compared with normal coronary arteries.

Since RANTES is a ligand for the chemokine receptors CCR1 and CCR5, then these receptors, located on circulating mononuclear cells, may be useful therapeutic targets in transplantation biology. The importance of the CCR1 receptor was examined in heart transplantation models in mice carrying a targeted deletion in the CCR1 gene (Gao, W. et al., *J. Clin. Invest* (2000), Vol. 105, pp. 35–44). In this study, four separate models of allograft survival showed significant prolongation by CCR1 (−/−) recipients. In one model, levels of cyclosporin A that had marginal effects in CCR1 (+/+) mice resulted in permanent allograft acceptance in CCR1 (−/−) recipients.

Certain small molecules have recently been shown to be non-peptide CCR1 receptor antagonists by inhibiting the activity of RANTES and MIP-1α and are therefore useful as anti-inflammatory agents. See PCT Published patent application Ser. No. WO 98/56771, U.S. patent application, Ser. No. 09/094,397, filed Jun. 9, 1998, now U.S. Pat. No. 6,207,665, issued Mar. 27, 2001, Hesselgesser, J. et al, *J. Biol. Chem.* (1998), Vol. 273, pp. 15687–15692, Ng, H. P. et al, *J. Med. Chem.* (1999), Vol. 42, pp. 4680–4694, Liang, M. et al., *Eur. J. Pharmacol* (2000a), Vol. 389, pp. 41–49, and Liang, M. et al, *J. Biol. Chem.* (2000b), Vol. 275, pp. 19000–19008. The disclosures of these patent applications and journal articles are incorporated in full by reference herein.

Cyclosporins are a family of neutral lipophilic cyclic oligopeptides (11-mers) produced from the fungus *Tolypocladium inflatum* Gams, as well as other fungi imperfecti. The major component is cyclosporin A, a well-known commercially available immunosuppressive drug that selectively inhibits adaptive immune responses by blocking T cell activation (see Kahan, B. D., *New Engl. J. Med.* (1989), Vol. 321, pp. 1725–1738, and Valantine, H., *Transplant Proc.* (2000), Vol. 32, pp. 27S–44S). Although cyclosporin A has been a critical factor in the success of organ transplantation, there remains major long-term safety problems directly associated with cyclosporin A-based immunosuppression, including nephrotoxicity, hypertension, diabetes mellitus and post-transplant lymphoproliferative disease. It would therefore be desirable to be able to administer a sub-nephrotoxic dose of cyclosporin A, thereby reducing its unwanted side effects, while maintaining the immunosuppressive activity necessary to avoid chronic rejection, which, in the case of heart transplantation, is known as chronic allograft vasculopathy, principally manifested as accelerated arteriosclerosis.

Related Disclosures

In a recent renal transplant study, the peptide chemokine receptor antagonist Met-RANTES, when given with low doses of cyclosporin A, significantly reduced renal injury, including interstitial inflammation, mainly by reducing the number of infiltrating monocytes (Gröne, H. J. et al., *FASEB J.* (1999), Vol. 13, pp. 1371–1383). This study supports the theory that RANTES, through activation of specific chemokine receptors on mononuclear cells, plays an important role in allograft rejection.

Published European Patent Application 1 000 626 (Applied Research Systems) discloses the use of a peptide chemokine receptor antagonist, Met-RANTES, together with a cyclosporin for treating or preventing rejection of transplanted organs, tissues or cells.

SUMMARY OF THE INVENTION

This invention is directed to pharmaceutical compositions useful in treating heart transplant rejection in mammals, which compositions comprise one or more pharmaceutically acceptable excipients, a therapeutically effective amount of a non-peptide CCR1 receptor antagonist and a sub-nephrotoxic amount of cyclosporin A. In particular, this invention is directed to pharmaceutical compositions useful in treating transplant rejection in mammals, which compositions comprise one or more pharmaceutically acceptable excipients, a sub-nephrotoxic amount of cyclosporin A and a therapeutically effective amount of a non-peptide CCR1 receptor antagonist selected from the compounds disclosed in U.S. Pat. No. 6,207,665.

This invention is also directed to methods of administering to a mammal in need thereof a pharmaceutical composition useful in treating heart transplant rejection in mammals, which composition comprises one or more pharmaceutically acceptable excipients, a therapeutically effective amount of a non-peptide CCR1 receptor antagonist and a sub-nephrotoxic amount of cyclosporin A. In particular, this invention is directed to methods of administering to a mammal in need thereof a pharmaceutical composition useful in treating heart transplant rejection in mammals, which composition comprises one or more pharmaceutically acceptable excipients, a sub-nephrotoxic amount of cyclosporin A, and a therapeutically effective amount of a non-peptide CCR1 receptor antagonist selected from the disclosed in U.S. Pat. No. 6,207,665.

This invention is also directed to methods of treating heart transplant rejection in a mammal which method comprises administering to a mammal in need thereof a pharmaceutical composition comprising one or more pharmaceutically acceptable excipients, a therapeutically effective amount of a non-peptide CCR1 receptor antagonist and a sub-nephrotoxic amount of cyclosporin A. In particular, this invention is directed to methods treating heart transplant rejection in a mammal which method comprises administering to a mammal in need thereof a pharmaceutical composition comprising one or more pharmaceutically acceptable excipients, a sub-nephrotoxic amount of cyclosporin A, and a therapeutically effective amount of a non-peptide CCR1 receptor antagonist selected from the compounds disclosed in U.S. Pat. No. 6,207,665.

BRIEF DESCRIPTION OF THE DRAWINGS

FIG. 5 shows the effect of combinations of a non-peptide CCR1 receptor antagonist of the invention and cyclosporin A on rejection score in rats 3 days after receiving allogeneic heart transplants.

DETAILED DESCRIPTION OF THE INVENTION

A. Definitions

Figure 1:
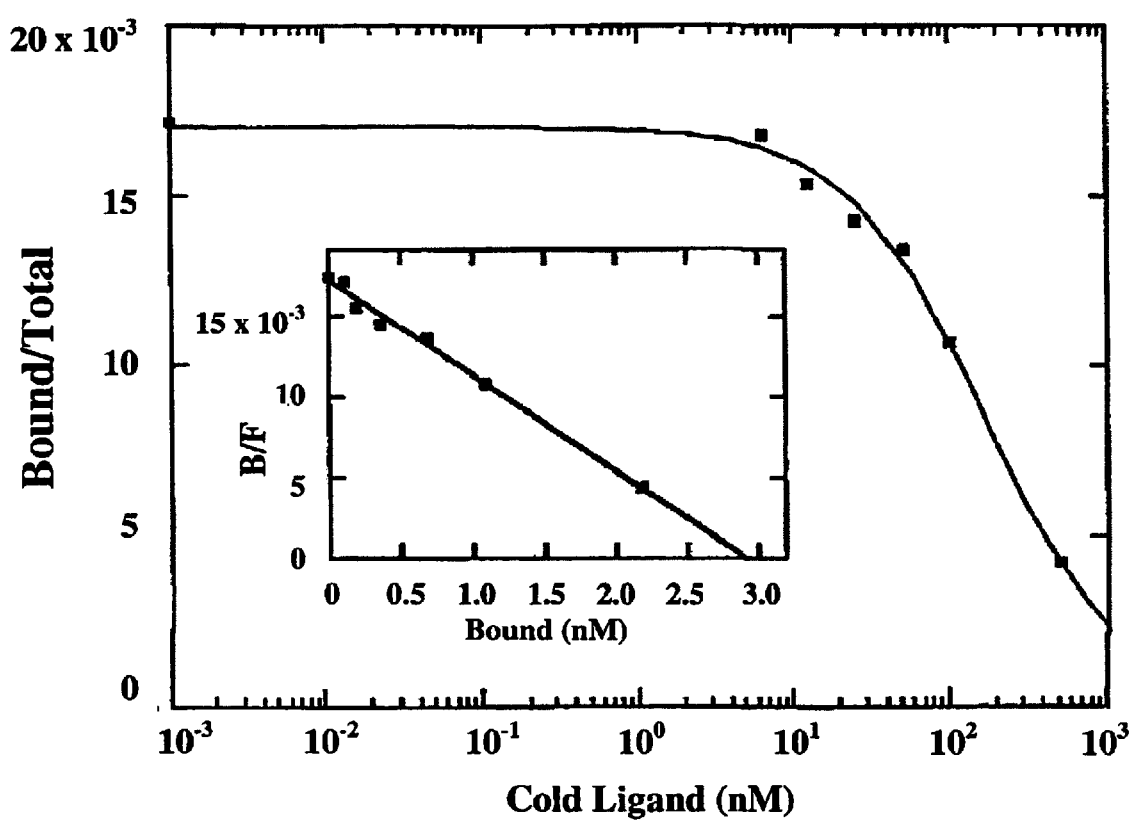
FIG. 1 shows the effect of a non-peptide CCR1 receptor antagonist of the invention on binding of radiolabeled MIP-1α to rat CCR1 expressing cells.

As used in the specification and appended claims, unless specified to the contrary, the following terms have the meaning indicated:

"Aminocarbonyl" refers to the radical —C(O)NH$_2$.

"Phenyl" refers to the benzene radical optionally substituted by one or more substituents selected from the group consisting of hydroxy, halo, alkyl, haloalkyl, alkoxy, alkenyl, nitro, cyano, amino, monoalkylamino, dialkylamino, alkylcarbonyl, carboxy, alkoxycarbonyl, and aminocarbonyl.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, propionic acid, pyruvic acid, maleic acid, malonic acid, succinic acid, fumaric acid, tartaric acid, citric acid, benzoic acid, mandelic acid, methanesulfonic acid, ethanesulfonic acid, p-toluenesulfonic acid, salicylic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, zinc, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

"Ureido" refers to a radical of the formula —N(H)—C(O)—NH$_2$.

It is understood from the above definitions and examples that for radicals containing a substituted alkyl group any substitution thereon can occur on any carbon of the alkyl group.

"Heart transplant rejection" refers to those disease-states, for the purposes of this invention, which are characterized by acute or chronic post-operation rejection of a heart transplant and includes: early graft failure, early acute rejection, early systemic rejection, and late chronic allograft vasculopathy (early and late are defined as less and more than six months to one year post-transplantation, respectively).

"Mammal" includes humans and domesticated animals, such as cats, dogs, swine, cattle, sheep, goats, horses, rabbits, and the like.

"Sub-nephrotoxic amount" refers to an amount of a cyclosporin A that is a therapeutically effective amount for treating heart transplant rejection in a human, but that is not associated with the unwanted side effect of nephrotoxicity, which is characterized by increased serum creatinine, increased proteinuria, increased fluid retention, decreased glomerular filtration rate, and decreased sodium and potassium excretion.

"Simultaneously" refers to the use of pharmaceutical compositions comprising two active ingredients, a therapeutically effective amount of a non-peptide CCR1 receptor antagonist of the invention and a sub-nephrotoxic amount of cyclosporin A, in the presence of one or more pharmaceutically acceptable excipients, in a single formulation.

"Sequentially" refers to the use of pharmaceutical compositions of the invention in two different formulations, each comprising one of the two active ingredients, a therapeutically effective amount of a non-peptide CCR1 receptor antagonist of the invention or a sub-nephrotoxic amount of cyclosporin A, together with one or more pharmaceutically acceptable excipients. The two formulations are administered to a mammal in need thereof at different times.

The non-peptide CCR1 receptor antagonists of the invention may have asymmetric carbon atoms in their structure. The non-peptide CCR1 receptor antagonists may therefore exist as single stereoisomers, racemates, and as mixtures of enantiomers and diastereomers. All such single stereoisomers, racemates and mixtures thereof are intended to be within the scope of this invention. Absolute configuration of certain carbon atoms within the non-peptide CCR1 receptor antagonists, if known, is indicated by the appropriate absolute descriptor R or S. The descriptor "trans" is used to indicate that the $R^{1a}$ substituents are on opposite sides of the piperazine plane.

The descriptor "cis" is used to indicate that the $R^{1a}$ substituents are on the same side of the piperazine plane.

The nomenclature for the non-peptide CCR1 receptor antagonists of the invention used herein is a modified form of the I.U.P.A.C. system wherein the non-peptide CCR1 receptor antagonists contemplated to be within the invention are named as piperazine derivatives, as described in U.S. Pat. No. 6,207,665.

"Therapeutically effective amount" refers to that amount of a non-peptide CCR1 receptor antagonist, preferably a non-peptide CCR1 receptor antagonist of formula (I) as described below, which, when administered to a mammal in need thereof, preferably a human, is sufficient to effect treatment, as defined below, for heart transplant rejection. The amount of non-peptide CCR1 receptor antagonist of the invention which constitutes a "therapeutically effective amount" will vary depending on the non-peptide CCR1 receptor antagonist utilized, the severity of the rejection, and the age of the human to be treated, but can be determined routinely by one of ordinary skill in the art having regard to his own knowledge and to this disclosure.

"Treating" or "treatment" as used herein covers the treatment of heart transplant rejection in a mammal, preferably a human, and includes:

(i) preventing the rejection from occurring in a mammal, preferably a human, in particular, prior to or subsequent to a heart transplant in such mammal;

(ii) inhibiting the condition, i.e., arresting development of rejection; or (iii) relieving the condition, i.e., causing regression of the rejection.

B. Preferred Embodiments

Of the pharmaceutical compositions described above in the Summary of the Invention, a preferred group of pharmaceutical compositions include those compositions wherein the non-peptide CCR1 receptor antagonist is a compound selected from formula (I):

(I)

R³—R⁴—R⁵—R⁶—N—R¹ᵃ—⟨benzyl⟩—R² wherein:
R¹ᵃ is one or more substituents independently selected from the group consisting of alkyl or hydroxyalkyl;
R² is fluoro at the 4-position;
R³ is phenyl substituted at the 4-position with chloro and at the 2-position by aminocarbonyl, ureido or glycinamido;
R⁴ is —O—;
R⁵ is methylene; and
R⁶ is —C(O)—;
as a single stereoisomer or a mixture thereof; or a pharmaceutically acceptable salt thereof.

Of this group of pharmaceutical compositions, a preferred subgroup of pharmaceutical compositions include those compositions wherein the non-peptide CCR1 receptor antagonist is selected from the group consisting of:

(2R,5S)-1-((4-chloro-2-(aminocarbonyl)phenoxy)methyl) carbonyl-2,5-dimethyl-4-(4-fluorobenzyl)piperazine;
(trans)-1-((4-chloro-2-(glycinamido)phenoxy)methyl) carbonyl-2,5-dimethyl-4-(4-fluorobenzyl)piperazine;
(2R)-1-((4-chloro-2-(ureido)phenoxy)methyl)carbonyl-2-methyl-4-(4-fluorobenzyl)piperazine;
(trans)-1-((4-chloro-2-(ureido)phenoxy)methyl)carbonyl-2,5-dimethyl-4-(4-fluorobenzyl)piperazine; (2R,5S)-1-((4-chloro-2-(ureido) phenoxy)methyl)carbonyl-2,5-dimethyl-4-(4-fluorobenzyl)piperazine; and
(2R, 5S)-1-((4-chloro-2-(glycinamido)phenoxy)methyl) carbonyl-2,5-dimethyl-4-(4-fluorobenzyl)piperazine.

Of this group of pharmaceutical compositions, another preferred subgroup of pharmaceutical compositions include those compositions wherein the non-peptide CCR1 receptor antagonist is (2R)-1-((4-chloro-2-(ureido)phenoxy)methyl) carbonyl-2-methyl-4-(4-fluorobenzyl)piperazine Of this subgroup of pharmaceutical compositions, a preferred class of pharmaceutical compositions include those compositions wherein the mammal in need thereof is a human.

Of the methods of administration as described above in the Summary of the Invention, a preferred group of methods include those methods wherein the non-peptide CCR1 receptor antagonist and the cyclosporin A are administered to the mammal in need thereof simultaneously or sequentially.

Of this group of methods, a preferred subgroup of methods include those methods wherein the non-peptide CCR1 receptor antagonist is a compound selected from formula (I):

(I)

R³—R⁴—R⁵—R⁶—N—R¹ᵃ—⟨benzyl⟩—R² wherein:
R¹ᵃ is one or more substituents independently selected from the group consisting of alkyl or hydroxyalkyl;
R² is fluoro at the 4-position;
R³ is phenyl substituted at the 4-position with chloro and at the 2-position by aminocarbonyl, ureido or glycinamido;
R⁴ is —O—;
R⁵ is methylene; and
R⁶ is —C(O)—;
as a single stereoisomer or a mixture thereof; or a pharmaceutically acceptable salt thereof.

Of this subgroup of methods, a preferred class of methods include those wherein the non-peptide CCR1 receptor antagonist is selected from the group consisting of:

(2R,5S)-1-((4-chloro-2-(aminocarbonyl)phenoxy)methyl) carbonyl-2,5-dimethyl-4-(4-fluorobenzyl)piperazine;
(trans)-1-((4-chloro-2-(glycinamido)phenoxy)methyl) carbonyl-2,5-dimethyl-4-(4-fluorobenzyl)piperazine;
(2R)-1-((4-chloro-2-(ureido)phenoxy)methyl)carbonyl-2-methyl-4-(4-fluorobenzyl)piperazine;
(trans)-1-((4-chloro-2-(ureido)phenoxy)methyl)carbonyl-2, 5-dimethyl-4-(4-fluorobenzyl)piperazine;
(2R,5S)-1-((4-chloro-2-(ureido)phenoxy)methyl)carbonyl-2,5-dimethyl-4-(4-fluorobenzyl)piperazine; and
(2R,5S)-1-((4-chloro-2-(glycinamido)phenoxy)methyl) carbonyl-2,5-dimethyl-4-fluorobenzyl)piperazine.

Of this subgroup of methods, another preferred class of methods include those methods wherein the non-peptide CCR1 receptor antagonist is (2R)-1-((4-chloro-2-(ureido) phenoxy)methyl)carbonyl-2-methyl-4-(4-fluorobenzyl) piperazine.

Of this class of methods, a preferred subclass of methods include those methods wherein the mammal in need thereof is a human.

Of the methods of treatment described above in the Summary of the Invention, a preferred group of methods include those methods wherein the non-peptide CCR1 receptor antagonist is a compound selected formula (I):

(I)

R³—R⁴—R⁵—R⁶—N—R¹ᵃ—⟨benzyl⟩—R² wherein:
R¹ᵃ is one or more substituents independently selected from the group consisting of alkyl or hydroxyalkyl;
R² is fluoro at the 4-position;
R³ is phenyl substituted at the 4-position with chloro and at the 2-position by aminocarbonyl, ureido or glycinamido;
R⁴ is —O—;
R⁵ is methylene; and
R⁶ is —C(O)—;
as a single stereoisomer or a mixture thereof; or a pharmaceutically acceptable salt thereof.

Of this group of methods, a preferred subgroup of methods include those methods wherein the non-peptide CCR1 receptor antagonist is selected from the group consisting of:

(2R,5S)-1-((4-chloro-2-(aminocarbonyl)phenoxy)methyl) carbonyl-2,5-dimethyl-4-(4-fluorobenzyl)piperazine;
(trans)-1-((4-chloro-2-(glycinamido)phenoxy)methyl) carbonyl-2,5-dimethyl-4-(4-fluorobenzyl)piperazine;

(2R)-1-((4-chloro-2-(ureido)phenoxy)methyl)carbonyl-2-methyl-4-(4-fluorobenzyl)piperazine;
(trans)-1-((4-chloro-2-(ureido)phenoxy)methyl)carbonyl-2,5-dimethyl-4-(4-fluorobenzyl)piperazine;
(2R,5S)-1-((4-chloro-2-(ureido)phenoxy)methyl)carbonyl-2,5-dimethyl-4-(4-fluorobenzyl)piperazine; and
(2R,5S)-1-((4-chloro-2-(glycinamido)phenoxy)methyl)carbonyl-2,5-dimethyl-4-(4-fluorobenzyl)piperazine.

Of this group of methods, another preferred subgroup of methods include those methods wherein the non-peptide CCR1 receptor antagonist is (2R)-1-((4-chloro-2-(ureido)phenoxy)methyl)carbonyl-2-methyl-4-(4-fluorobenzyl)piperazine.

Of this subgroup of methods, a preferred class of methods include those methods wherein the mammal in need thereof is a human.

Of this subgroup of methods, another preferred class of methods include those methods wherein the non-peptide CCR1 receptor antagonist and the cyclosporin A are administered to the mammal in need thereof simultaneously or sequentially.

C. Utility of the Compositions of the Invention

The pharmaceutical compositions disclosed herein are useful for treating heart transplant rejection in mammals, preferably humans.

It has been shown that cyclosporin A is very effective in the management of graft failure, acute rejection and systemic rejection in the first year following heart transplantation. However, long-term maintenance use of cyclosporin A, although effective in the management of chronic allograft vasculopathy, is directly associated with side effects, including nephrotoxicity, hypertension, diabetes mellitus and post-transplant lymphoproliferative disease.

It has been shown that inhibition of the activity of certain chemokines or their receptors can be effective in animal models of organ transplantation. As described above, in a recent renal transplant study in rats the chemokine receptor antagonist Met-RANTES when given with low doses of cyclosporin A significantly reduced renal injury including interstitial inflammation mainly by reducing the number of infiltrating monocytes (Grone, H. J. et al, (1999), supra). In another study, the importance of the CCR1 receptor was examined in heart transplantation models in mice carrying a targeted deletion of CCR1 (Gao, W. et al, (2000), supra). In this study four separate models of allograft survival showed significant prolongation by CCR1(-/-) recipients. In one model levels of cyclosporin A that had marginal effects in CCR1(+/+) mice resulted in permanent allograft acceptance in CCR1(-/-) recipients.

Based on these studies there is strong evidence to support the theory that the chemokine RANTES, acting through the CCR1 receptor, plays an important role in organ transplant rejection. The non-peptide CCR1 receptor antagonists of the invention have been shown to inhibit the activity of RANTES. Therefore, the non-peptide CCR1 receptor antagonists of the invention are useful in treating organ transplant rejection, particularly heart transplant rejection.

As discussed in more detail below, the non-peptide CCR1 receptor antagonists of the invention in combination with cyclosporin A displayed unexpected results in treating heart transplant rejection in mammals. In particular, the combination of a therapeutically effective amount of a non-peptide CCR1 receptor antagonist and a sub-nephrotoxic amount of cyclosporin A demonstrate the ability to treat heart transplant rejection without the unwanted nephrotoxic effect of cyclosporin A.

D. Testing of the Compounds of the Invention

To demonstrate that the non-peptide CCR1 receptor antagonists of the invention inhibit the activity of the chemokines MIP-1α or RANTES acting through the CCR1 receptor several in vitro assays may be employed that have been previously described. See, e.g., U.S. Pat. No. 6,207,665 and Hesselgesser, J. et al., (1998), supra, Ng, H. P. et al., (1999), supra, Liang, M. et al., (2000a), supra, and Liang, M. et al., (2000b), supra.

Figure 2:
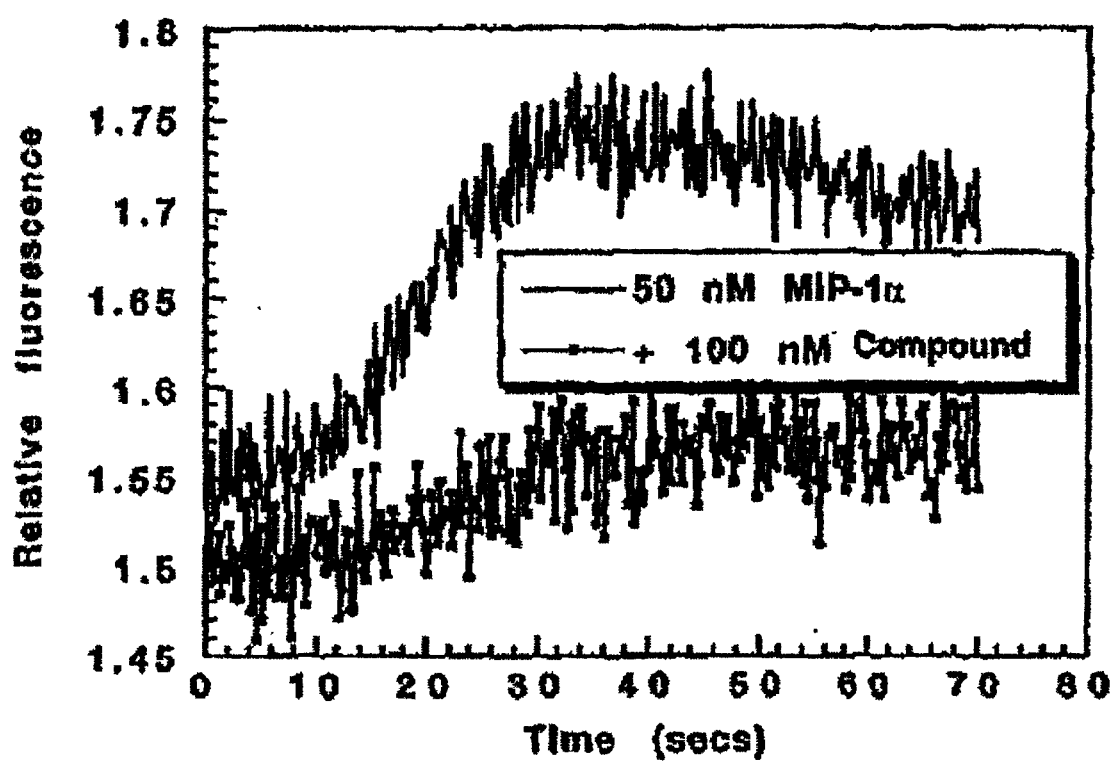
FIG. 2 shows the effect of a non-peptide CCR1 receptor antagonist of the invention on the MIP-1α induced rise in intracellular $Ca^{2+}$ in rat CCR1 expressing cells.

A non-peptide CCR1 receptor antagonist disclosed in U.S. Pat. No. 6,207,665, i.e., (2R)-1-((4-chloro-2-(ureido)phenoxy)methyl)carbonyl-2-methyl-4-(4-fluorobenzyl)piperazine, was tested for binding to the rat CCR1 receptor by in vitro binding assays described in Example 1, the results of which are illustrated in FIG. 1. Scatchard analysis of displacement binding studies revealed that the affinity of the non-peptide CCR1 receptor antagonist was 121±60 nM (see FIG. 1), approximately 100 times less effective for the rat CCR1 receptor than for the human CCR1 receptor ($K_i$=1 nM). In addition, this non-peptide CCR1 receptor antagonist was able to competitively displace radiolabeled RANTES from the rat CCR1 receptor with a similar $K_i$. The same non-peptide CCR1 receptor antagonist was shown to be a functional in vitro antagonist of the rat CCR1 receptor by performing calcium flux assays described below in Example 2 and FIG. 2. The transient rise in intracellular $Ca^{2++}$ concentration induced by 50 nM MIP-1α was inhibited by pre-incubating rat CCR1 receptor expressing cells with 100 nM of the non-peptide CCR1 receptor antagonist ("Compound" in FIG. 2). These data demonstrated that although the non-peptide CCR1 receptor antagonist was not as potent an inhibitor of the rat CCR1 receptor as compared to the human CCR1 receptor, the non-peptide CCR1 receptor antagonist was able to compete effectively for binding to, and was a potent functional antagonist of, the rat CCR1 receptor in vitro.

Figure 3:
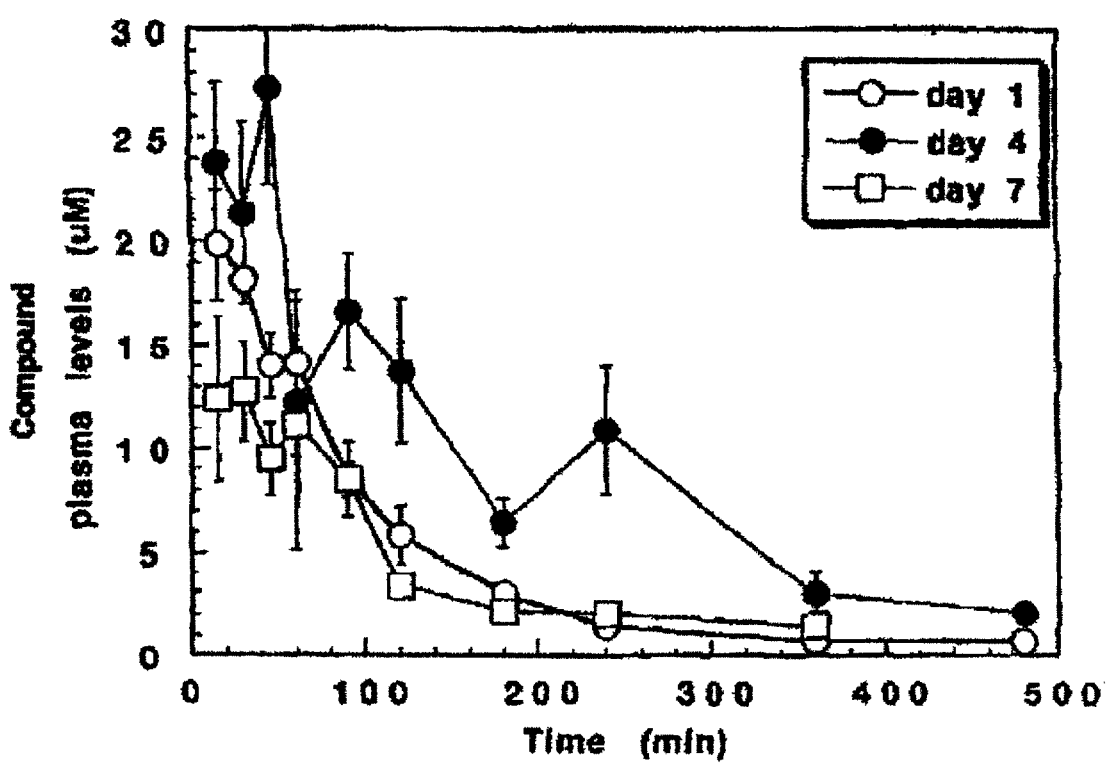
FIG. 3 shows the plasma concentrations of a non-peptide CCR1 receptor antagonist of the invention following chronic subcutaneous dosing in rats.

Pharmacokinetic studies were carried out in rats with a non-peptide CCR1 receptor antagonist of the invention, as described below in Example 3 and FIG. 3. Peak plasma levels 1, 4 and 7 days following the subcutaneous administration of the non-peptide CCR1 receptor antagonist varied between 12 and 27 $\mu$M (see FIG. 3). Absorption was relatively rapid with significant plasma levels observed at 15 minutes post-drug exposure. After 8 hours plasma drug levels were approximately 1 to 2 $\mu$M. The plasma half-life ranged between 2 to 3 hours. Though there did not appear to be any pattern of either enhanced clearance or accumulation of the non-peptide CCR1 receptor antagonist on repeated subcutaneous dosing, a considerable amount of variability was observed in the rate and extent of drug absorption on all of the days measured. These studies showed that subcutaneous dosing of a non-peptide CCR1 receptor antagonist of the invention at 50 mg/kg three times per day provided adequate drug levels over a 24 hour period.

Figure 4:
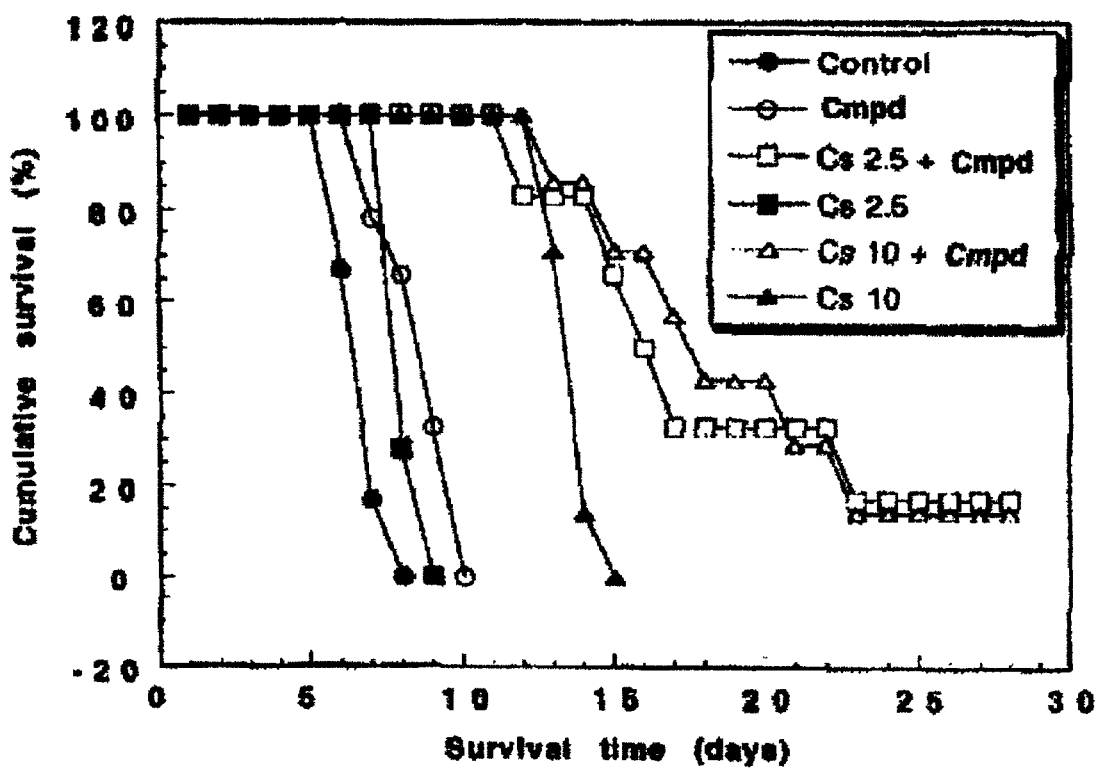
FIG. 4 shows the effect of combinations of a non-peptide CCR1 receptor antagonist of the invention and cyclosporin A on survival of allogeneic heart transplants in rats.

An in vivo assay which may be employed to demonstrate the usefulness of the pharmaceutical compositions of the invention in treating heart transplant rejection in mammals is the rat heterotopic heart transplant rejection model (see, e.g., Nisco, S. et al., *J. Immunol.* (1994), Vol. 152, pp. 3786–3792, and Ono, K. et al., *J. Thorac. Cardiovasc. Surg.* (1969), Vol. 57, pp. 225–229.) The pharmaceutical compositions of the invention were tested in an in vivo assay described below in Example 4, the results of which are illustrated in FIG. 4. In this assay an increase in allograft survival time corresponds to a decrease in heart transplant rejection in the recipient Lewis rats given donor ACI rat grafts. The mean allograft survival time of animals given only the non-peptide CCR1 receptor antagonist, i.e. (2R)-1-((4-chloro-2-(ureido)phenoxy)methyl) carbonyl-2-methyl-4-(4-fluorobenzyl)piperazine ("Cmpd" in FIG. 4), in vehicle was 8.8±1.2 days compared to 6.8±0.8 days for vehicle-treated animals ("Control" in FIG. 4). The mean allograft survival time of the animals treated with a non-peptide CCR1 receptor antagonist of the invention was statistically significant at the 0.05 level with respect to the survival time of the control groups and Log rank analysis of survival test gave a p=0.0048 for animals receiving the non-peptide CCR1 receptor antagonist as compared to control.

Assays were performed in which animals were treated with a therapeutically effective amount of a non-peptide CCR1 receptor antagonist of the invention, i.e., (2R)-1-((4-chloro-2-(ureido)phenoxy) methyl)carbonyl-2-methyl-4-(4-fluorobenzyl)piperazine, and a sub-nephrotoxic amount (2.5 mg/kg) of cyclosporin A. The mean allograft survival time of animals given only 2.5 mg/kg cyclosporin A ("Cs 2.5" in FIG. 4) was 7.3±0.5 days compared to 17.5±5.9 days for animals on the same protocol that were additionally treated with the non-peptide CCR1 receptor antagonist ("Cs 2.5+ Cmpd" in FIG. 4). The mean allograft survival time of animals given a therapeutic dose of cyclosporin A, 10 mg/kg ("Cs 10" in FIG. 4), was 12.9±0.7 days compared to 18.4±5.4 days for animals on the same protocol that were additionally treated with the non-peptide CCR1 receptor antagonist ("Cs 10+Cmpd" in FIG. 4). The mean survival times of the animals treated with either 2.5 or 10 mg/kg cyclosporin A plus the non-peptide CCR1 receptor antagonist were statistically significant from the mean survival times of the animals treated with either 2.5 mg/kg or 10 mg/kg cyclosporin A alone with values of p=0.0009 and p=0.0148, respectively.

Light microscopy and immunohistology for infiltrating monocytes, as described below in Example 5 and FIG. 5, confirmed these survival data. Three days after transplantation the rejection score was significantly reduced by the combined treatment of the non-peptide CCR1 receptor antagonist of the invention as described above and cyclosporin A ("Compound-Cyclosporin A" in FIG. 5). In non-immunosuppressed transplants a dense mononuclear infiltrate was observed. Many cardiomyocytes were vacuolated or necrotic. Interstitial edema was pronounced. In the cyclosporin A treated rats the inflammatory cell infiltrate was reduced, though still clearly evident, specifically around venules with focal destruction of cardiomyocytes. The rats treated only with the non-peptide CCR1 receptor antagonist showed focal mononuclear cell infiltrates that were pronounced with similar morphology to those observed in non-immunosuppressed transplants. The animals treated with both the non-peptide CCR1 receptor antagonist and cyclosporin A showed well-preserved cardiac morphology with sparse mononuclear cell infiltrates. In non-immunosuppressed transplants many cells of the dense mononuclear cell infiltrate consisted of monocytes/macrophages which were closely juxtaposed to the cardiomyocytes. In the cyclosporin A treated rats the inflammatory cell infiltrate was focal and was composed primarily of ED-1 positive cells. In the non-peptide CCR1 receptor antagonist treated animals the mononuclear cell infiltrate varied significantly; areas with moderately dense monocytic infiltrate around venules were seen. The combined treatment of the non-peptide CCR1 receptor antagonist and cyclosporin A resulted in a dramatic reduction in monocyte/macrophage infiltration into the allogenic rat hearts. Based on the data from these studies, the non-peptide CCR1 receptor antagonist of the invention given in combination with cyclosporin A resulted in a clear synergistic increase in efficacy in heart transplantation compared to non-peptide CCR1 receptor antagonist or cyclosporin A alone.

Figure 6:
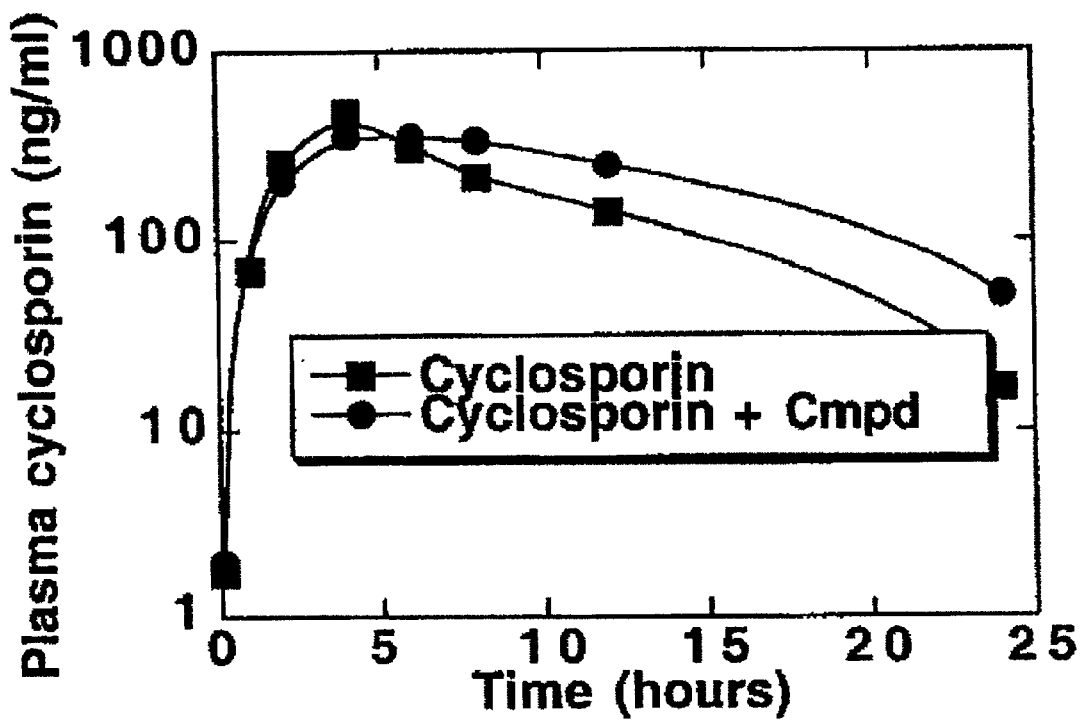
FIG. 6 shows the effect of a non-peptide CCR1 receptor antagonist of the invention on the plasma levels of cyclosporin A in rats.

Although the combination of a non-peptide CCR1 receptor antagonist and cyclosporin A resulted in a clear synergistic increase in heart transplant survival, it remained a possibility that the effect seen was due to drug/drug interactions that stabilize blood cyclosporin A levels rather than true synergism of the drug combination. Pharmacokinetic studies were performed to measure the blood levels of cyclosporin A in rats in the absence or presence of a non-peptide CCR1 receptor antagonist of the invention, i.e., (2R)-1-((4-chloro-2-(ureido)phenoxy)methyl)carbonyl-2-methyl-4-(4-fluorobenzyl)piperazine, as described below in Example 6 and FIG. 6. Visual inspection of the time-concentration curves suggested a slight prolongation of the blood half-life of cyclosporin A in rats treated with the non-peptide CCR1 receptor antagonist ("Cmpd" in FIG. 6). However, statistical analysis of the paired groups indicated that there was no significant difference between the two parameters calculated (P-value for AUC=0.224 and for $T_{1/2}$=0.317). Therefore, drug/drug interactions can be ruled out as the basis for the clear synergistic increase in heart transplant survival in rats treated with a combination of a non-peptide CCR1 receptor antagonist of the invention and cyclosporin A.

Figure 7:
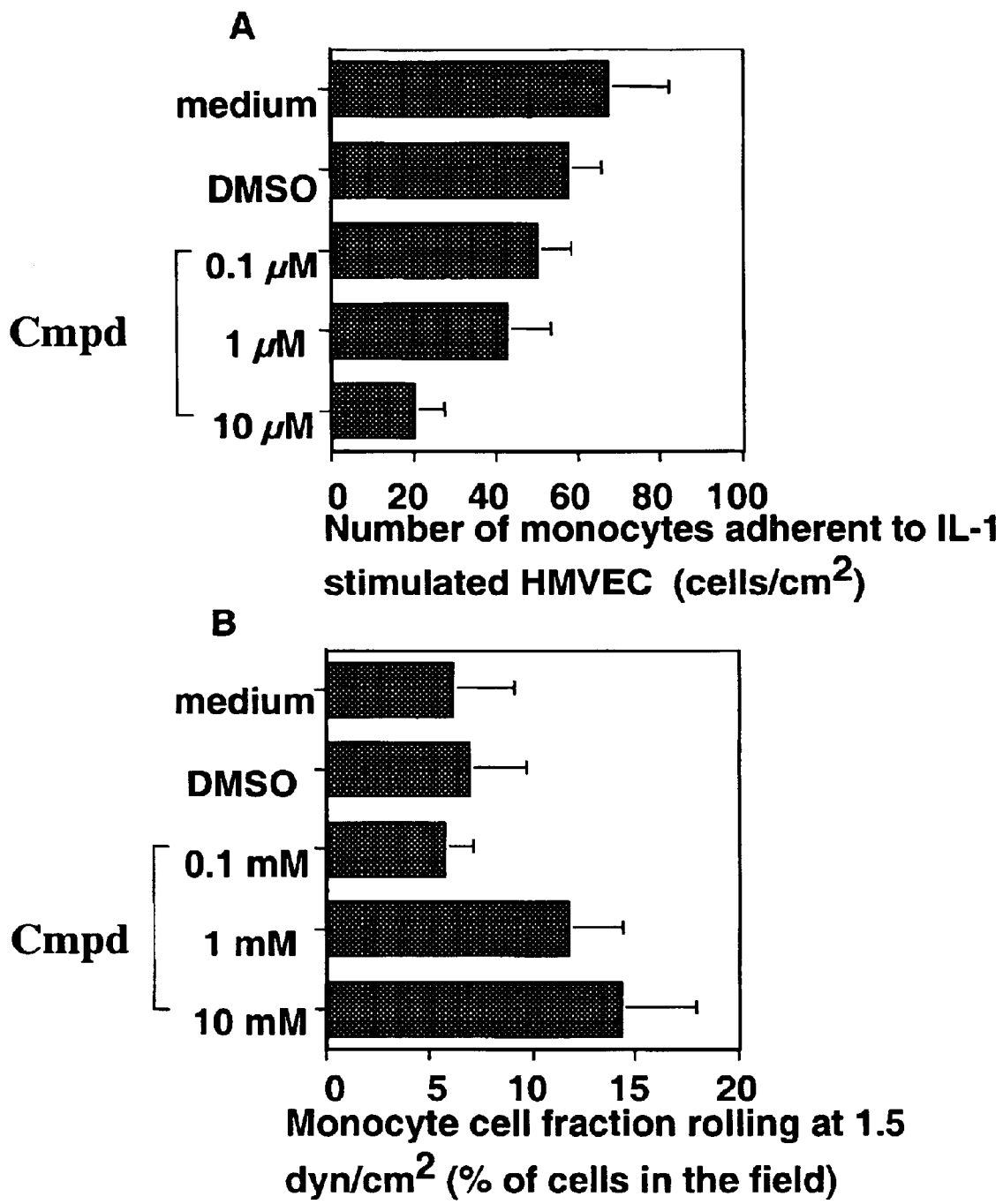
FIG. 7 shows the effect of a non-peptide CCR1 receptor antagonist of the invention on the adhesion of monocytes to activated endothelial cells.

In vitro adhesion and rolling assays were performed to determine whether the dramatic reduction in monocyte/macrophage infiltration into the allogeneic rat hearts may be due, at least in part, to the inhibition of chemokines acting through the CCR1 receptor. Previous work showed that monocytic cells display increased attachment to IL-1β-activated endothelial cells that bind RANTES following preincubation with exogenous RANTES for 30 minutes (Gr one, H. J. et al., (1999), supra). Isolated human blood monocytes were treated with increasing amounts of a non-peptide CCR1 receptor antagonist of the invention, i.e., (2R)-1-((4-chloro-2-(ureido)phenoxy)methyl)carbonyl-2-methyl-4-(4-fluorobenzyl)piperazine, and the attachment to microvascular endothelial cells was carried out as described below in Example 7 and FIG. 7. The RANTES-mediated and shear-resistant adhesion of monocytes to IL-1β-activated microvascular endothelial cells was dose-dependently inhibited by the non-peptide CCR1 receptor antagonist ("Cmpd" in FIG. 7A). The percentage of monocytes that were found to undergo rolling or maintain rolling interactions, which serves as an inverse measure for monocyte arrest, was also dose-dependently inhibited by the non-peptide CCR1 receptor antagonist ("Cmpd" in FIG. 7B). These data strongly support the concept of true synergism of the combination of a non-peptide CCR1 receptor antagonist of the invention and cyclosporin A in treating heart transplant rejection in animals.

E. Administration of the Compositions of the Invention

Administration of the pharmaceutical compositions of the invention can be carried out via any of the accepted modes of administration or agents for serving similar utilities. Thus, administration can be, for example, orally, nasally, parenterally, topically, transdermally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages. The compositions will include a conventional pharmaceutical carrier or excipient and a compound of the invention as the/an active agent, and, in addition, may include other medicinal agents, pharmaceutical agents, carriers, adjuvants, etc.

Generally, depending on the intended mode of administration, the pharmaceutical compositions will contain about 1% to about 99% by weight of the active ingredients of the compositions, i.e. the non-peptide CCR1 receptor antagonist or a pharmaceutically acceptable salt thereof and cyclosporin A, and 99% to 1% by weight of a suitable pharmaceutical excipient. Preferably, the composition will be about 5% to 75% by weight of the active ingredients, with the rest being suitable pharmaceutical excipients.

The preferred route of administration is oral, using a convenient daily dosage regimen, which can be adjusted according to the degree of severity of the rejection of the heart transplant. For such oral administration, a pharmaceutical composition of the invention is formed by the incorporation of one or more of the normally employed pharmaceutical excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such compositions take the form of solutions, suspensions, tablets, pills, capsules, powders, sustained release formulations and the like.

Preferably such pharmaceutical compositions will take the form of capsule, caplet or tablet and therefore will also contain a diluent such as lactose, sucrose, dicalcium phosphate, and the like; a disintegrant such as croscarmellose sodium or derivatives thereof; a lubricant such as magnesium stearate and the like; and a binder such as a starch, gum acacia, polyvinylpyrrolidone, gelatin, cellulose ether derivatives, and the like.

The pharmaceutical compositions of the invention may also be formulated into a suppository using, for example, about 0.5% to about 50% active ingredients disposed in a carrier that slowly dissolves within the body, e.g., polyoxyethylene glycols and polyethylene glycols (PEG), e.g., PEG 1000 (96%) and PEG 4000 (4%).

Liquid pharmaceutically administrable compositions can, for example, be prepared by dissolving, dispersing, etc., the pharmaceutical compositions of the invention (about 0.5% to about 20%) and optional pharmaceutical adjuvants in a carrier, such as, for example, water, saline, aqueous dextrose, glycerol, ethanol and the like, to thereby form a solution or suspension.

If desired, pharmaceutical compositions of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Actual methods which can be used to prepare the above compositions are known, or will be apparent, to those skilled in this art; for example, see *Remington's Pharmaceutical Sciences,* 18th Ed., (Mack Publishing Company, Easton, Pa., 1990). The pharmaceutical compositions to be administered will, in any event, contain one or more pharmaceutically acceptable excipients, therapeutically effective amount of a non-peptide CCR1 receptor antagonist of the invention and a sub-nephrotoxic amount of cyclosporin A for treatment of heart transplant rejection.

A therapeutically effective amount of a non-peptide CCR1 receptor antagonist, preferably a non-peptide CCR1 receptor antagonist of formula (I), will vary depending upon a variety of factors including the activity of the specific compound employed; the metabolic stability and length of action of the compound; the age, body weight, general health, sex, and diet of the patient; the mode and time of administration; the rate of excretion; the severity of the rejection process; and the host undergoing therapy. Generally, a therapeutically effective daily dose is from about 0.14 mg to about 14.3 mg/kg of body weight per day of a non-peptide CCR1 receptor antagonist of formula (I); preferably, from about 0.7 mg to about 10 mg/kg of body weight per day; and most preferably, from about 1.4 mg to about 7.2 mg/kg of body weight per day. For example, for administration to a 70 kg person, the dosage range would be from about 10 mg to about 1.0 gram per day of the non-peptide CCR1 receptor antagonist; preferably from about 50 mg to about 700 mg per day, and most preferably from about 100 mg to about 500 mg per day.

F. Preparation of the Compositions of the Invention

The non-peptide CCR1 receptor antagonists of the invention are prepared according to methods described in U.S. Pat. No. 6,207,665.

The cyclosporins of the invention are neutral lipophilic cyclic peptides (11-mers) produced from the fungus *Tolypocladium inflatum* Gams, as well as other fungi imperfecti. They are available for research purposes. Two preparations of cyclosporin A, Sandimmune® and Neoral® (Novartis), are currently used in treating human organ transplantation rejection.

The following examples are provided as a guide to assist in the practice of the invention, and are not intended as a limitation on the scope of the invention.

EXAMPLE 1

In Vitro Assay

In Vitro Binding Assay for Non-Peptide CCR1 Receptor Antagonists

This sassy demonstrates the affinities of the non-peptide CCR1 receptor antagonists of the invention, preferably a non-peptide CCR1 receptor antagonist of formula (I), for binding to the rat CCR1 receptor.

Reagents and Solutions:

Chemokines: MIP-1α and RANTES (Peprotech Inc.)
Cells: Rat peripheral blood mononuclear cells (PBMC) were isolated from whole blood from Lewis rats by ACCU-PAQUE™ (4.2% w/v dextran and 11.6% w/v sodium diatrizoate) (Accurate Chemical & Scientific Corp.) density centrifugation.
Ligand: 1281-MIP-1α and $^{125}$I-RANTES from New England Nuclear (specific activity is 2200 Ci/mmol, 25 μCi/vial) was reconstituted in 1 mL $H_2O$.
Assay buffer: 130 mM NaCl, 5 mM KCl, 1 mM $MnCl_2$, 50 mM Tris, 30 μg/ml bacitracin, 0.1% BSA, pH 7.4.
Wash buffer: Phosphate buffer solution (PBS)
Compounds of the Invention: The stock solution of the compounds was 1 mM in 100% DMSO. The highest concentration in the assay was 10 μM and may vary depending on the potency of the compounds. Serial 1:3 dilutions from the highest concentration were made with assay buffer. Six concentrations of each compound were typically screened to generate a dose curve from which the $K_i$ value was determined.

Assay procedure:
Assays were performed in 96-well v-bottom microtiter plates in a total volume of 100 μL.

Rat PBMC were washed once in PBS and resuspended in the assay buffer to about 0.2 to 1.0×10$^6$ cells/mL. Cells were incubated with $^{125}$I-MIP-1α or $^{125}$I-RANTES in the presence or absence of varying concentrations of unlabeled MIP-1α, RANTES, or compound at 4° C. for 30 minutes.

The reactions were terminated by removing aliquots from the cell suspension and separating cells from buffer by centrifugation through a silicon/paraffin oil mixture as described in Hesselgesser et al., (1998), supra.

The nonspecific binding was determined in the presence of 100 nM or 1 μM of unlabeled MIP-1α or RANTES. The concentrations of compounds in the assay were typically from 10 μM to 30 nM in 1:3 dilution, and the concentrations for more potent compounds were lower depending on the potency.

Calculations:

The dose curves of each compound with 6 concentration points were generated and the binding data were curve fitted with the computer program IGOR (Wavemetrios) to determine the affinity and number of sites.

The non-peptide CCR1 receptor antagonists of the invention, when tested in this assay, demonstrated their affinity to bind to the rat CCR1 receptor.

EXAMPLE 2

In Vitro Assay Calcium Flux

Functional in Vitro Assay for Non-Peptide CCR1 Receptor Antagonists

Since the CCR1 receptor responds to the binding of its ligands, MIP-1α and RANTES, by mobilizing free intracellular calcium, one can measure biological activity by calcium flux assays using the fluorescent dye Fura-2. In the following assay the ability of the non-peptide CCR1 receptor antagonists of the invention to block this biologic response was measured.

Protocol:

1) Rat PBMC were isolated as described in Example 1, pelleted by centrifugation, and resuspended in Hanks Ca$^{2+}$ (50 mL Hanks, 1.0 mL 1 M Hepes, 1.6 mL 500 mM CaCl$_2$, pH 7.4). The cells were washed twice in this media.

2) The cells were resuspended in media at a density of 1×10$^6$ cells/mL in the presence of a final concentration of 1.25 μM Fura-2 AM (Molecular Probes) (the stock solution was prepared by dissolving 50 μg of Fura-2 in 50 μL of DMSO).

3) The cells were incubated at 37° C. for 30 minutes in the presence or absence of various concentrations of the non-peptide CCR1 receptor antagonists of the invention. Cells were washed by centrifugation as above to remove free Fura-2. Cells were resuspended at 1×10$^6$ cells/mL. Cells were then aliquoted (2.0 mL) in a cuvette and placed in a PTI Deltascan Model 4000 spectrofluorimeter. The cells were stimulated with 50 nM MIP-1α (Peprotech Inc.) and Ca$^{2+}$ release was measured in the spectrofluorimeter as a function of time.

4) The data were corrected for nM Ca$^{2+}$ released by adding 100 μL of 0.1% Triton X-100 (for maximum values) followed by 100 μL of 500 mM EGTA, pH 8.5 (for minimum values).

The non-peptide CCR1 receptor antagonists of the invention, when tested in this assay, demonstrated their ability to inhibit Ca$^{2+}$ mobilization in response to the binding of MIP-1α to the rat CCR1 receptor.

EXAMPLE 3

In Vivo Assay

Pharmacokinetic Studies in Lewis Rats

Adult male, specific pathogen-free Lewis (RT1l) rats (Charles River, Boston) weighing 200 to 250 g were used in these studies.

A solution of 40% cyclodextrin was prepared by adding Cyclodextrin (400 g, Aldrich) into a 1 liter sterile plastic bottle. Unbuffered saline containing only sodium and potassium chloride was added and the mixture was shaken and mixed overnight to dissolve. Saline was added to a total volume of 1 liter. The solution was filtered through a 0.45 μm filter into a sterile bottle, labeled and stored at 4° C. A 25 mg/ml solution of compound in cyclodextrin was prepared by dissolving the compound into the 40% cyclodextrin in saline. The mixture was shaken followed by the addition of 230 μL of concentrated HCl. The mixture was stirred to dissolve. After dissolution was complete (1 hr) the pH of the solution was measured and 1 M KOH was added to raise the pH to 4.5. The solution was filtered through a 0.45 μm filter and stored at 4° C.

The non-peptide CCR1 receptor antagonists of the invention were prepared in a vehicle of 40% cyclodextrin/saline and rats were subcutaneously (s.c.) dosed (50 mg/kg three times per day) for seven days. Blood samples were collected by cardiac puncture in EDTA-containing tubes at various times, centrifuged and plasma was stored frozen until analyzed for drug levels.

Plasma samples were analyzed either by HPLC using UV detection methods or HPLC-MS (electrospray mode operated under a positive ion mode). Concentrations of the non-peptide CCR1 receptor antagonists of the invention were determined through a calibration curve constructed in plasma and analyzed under identical conditions. Related compounds were used as internal standards in these analyses.

HPLC-UV Method:

1) 100 μL aliquots of plasma samples were added to 200 μL ice cold acidic methanol (1% acetic acid) containing a fixed amount of an internal standard and mixed well.

2) The resulting protein precipitate was removed by centrifugation at 5,000× g and the supernatents were collected.

3) In parallel, control plasma samples were spiked with various amounts of the non-peptide CCR1 receptor antagonists of the invention, typically in the range of 0.3 to 25 μM, and processed as above.

4) The supernatents were evaporated to dryness in a vacuum evaporator, reconstituted with a 1:2 methanol:water solution (containing 0.1% TFA), vortexed for 30 sec and centrifuged to remove sediments.

5) The resulting supernatents were injected onto a YMC AQ ODS reversed phase column and analyzed under gradient HPLC conditions at a flow rate of 1 mL/min. The UV detector was set at 230 nm.

6) The gradient conditions were: initial, solvent A 22%/solvent B 78%; 2 min, solvent A 22%/solvent B 78%; 33 min solvent A 45%/solvent B 55%; 37 min solvent A 80%/solvent B 20%; 47 min solvent A 80%/solvent B 20%; 49 min, back to initial conditions.

7) Peak area ratios between the internal standard peak and the compound were calculated over the concentration range of the standard curve and this ratio was used to construct a calibration curve. The concentration of the compound of interest was derived from this curve by calculating the peak area ratio between the compound and internal standard peaks.

HPLC-MS Method:
1) The methodology used was similar to that described above, except that the sample preparation was stopped at the methanol precipitation step, and a short isocratic method was used instead of the gradient method.
2) A FISONS VG Platform single quadrupole instrument was used with an electrospray inlet operated at 3.57 kV. A YMC AQ ODS reversed phase column was employed under a flow rate of 1 mL/min with the total flow going into the UV detector at 214 nm.
3) The flow was split to infuse 50 $\mu$L/min into the mass spectrometer. Chromatograms were collected over a total run time of 7.5 min per sample with a 50 $\mu$L injection on the column. The ions were collected in a single ion positive ionization mode.
4) Quantitation was accomplished by integrating the area under the ion currents (control non-peptide CCR1 receptor antagonist of the invention and internal standards) and generating a calibration curve as described above.

The non-peptide CCR1 receptor antagonists of the invention, when tested in this assay, demonstrated adequate drug levels in rat plasma over a 24 hour period.

EXAMPLE 4

In Vivo Assay

Heterotopic Heart Transplant Rejection (Lewis or ACI Rats)

Adult male, specific pathogen-free ACI (RT1a) and Lewis (RT1l) rats (Charles River, Boston, Mass.) weighing 200 to 250 g were used as donors and recipients, respectively, in these studies. Vascularized cardiac allografts were heterotopically transplanted into the abdomen of recipient rats using a modification (Nisco, S. et al., (1994), supra) of the technique of Ono and Lindsay (Ono, K. et al., (1969), supra). End-to-side anastomoses were made from the ascending aorta of the donor heart to the abdominal aorta of the recipient and from the donor pulmonary artery to the recipient inferior vena cava, after the vena cava and pulmonary veins of the donor heart were ligated. Abdominal allografts were palpated on a daily basis to assess graft function, and rejection was deemed complete when palpable ventricular contractions ceased.

Cardiac allografts from ACI rats were heterotopically transplanted into the abdomen of recipient Lewis rats and these animals were given either: 40% cyclodextrin s.c. three times per day; 50 mg/kg of a non-peptide CCR1 receptor antagonist of the invention in 40% cyclodextrin s.c. three times per day; cyclosporin A in olive oil by gavage 10 mg/kg once per day for four days; cyclosporin A in olive oil by gavage 2.5 mg/kg once per day for the duration of the study; cyclosporin A in olive oil by gavage 10 mg/kg once per day for four days plus 50 mg/kg non-peptide CCR1 receptor antagonist in 40% cyclodextrin s.c. three times per day; or cyclosporin A in olive oil by gavage 2.5 mg/kg once per day for the duration of the study plus 50 mg/kg non-peptide CCR1 receptor antagonist in 40% cyclodextrin s.c. three times a day. The transplanted hearts were evaluated daily for signs of rejection over the course of the study.

The non-peptide CCR1 receptor antagonists of the invention, when tested in this assay, demonstrated the ability to significantly prolong heart transplant survival time when given in combination with cyclosporin A.

EXAMPLE 5

In Vivo Assay

Histology, Immunohistochemistry and Morphometry

Transplanted hearts were removed under deep anesthesia, quickly blotted free of blood, weighed, and then processed as needed for histology and immunohistochemistry. The organs were cut into 1-mm slices and either immersion-fixed in 4% formaldehyde in phosphate buffered saline (PBS) pH 7.35, (PBS: 99 mM NaH$_2$PO$_4$, 108 mM NaH$_2$PO$_4$ and 248 mM NaCl) for 24 h or fixed in methacarn for 8 h and embedded in paraffin. Light microscopy was performed on 3 $\mu$m sections stained by periodic acid-Schiff or Goldner-Elastica. Light microscopy was performed on allogeneic heart transplants 3 days after transplantation.

The ED1 monoclonal antibody (Serotec/Camon) was used on methacarn fixed paraffin embedded tissue (3 $\mu$m) to stain for rat monocytes/macrophage cells. An alkaline phosphatase anti-alkaline phosphatase detection system was used for visualization (Dako). Controls that omit the first or second antibody for each section were performed for negative staining. The immunohistologic stain for ED1-positive monocytes/macrophages in allogeneic heart transplants was performed 3 days after transplantation.

Histopathologic rejection in the allogeneic rat heart was graded according to Billingham (Billingham, M. E. In: *Cardiac transplantation*, pp. 133–152, Butterworths, Boston, 1990). Mild acute rejection (score: 1) was characterized by a sparse interstitial mononuclear infiltrate often accentuated in perivascular spaces. Moderate acute rejection (score: 2) was a moderately dense perimyocytic mononuclear infiltrate with some myocyte necrosis. Severe acute rejection (score: 3) featured a dense monocytic infiltrate with focal hemorrhage and replacement of myocytes and with occasional endothelialitis of intramural arteries. The rejection score was calculated for every tissue block and an average score was calculated from the different blocks for every transplanted heart as rejection processes tended to be focal.

The non-peptide CCR1 receptor antagonists of the invention, when tested in this assay, significantly reduced the rejection score and the extent of monocyte graft infiltration when given in combination with cyclosporin A.

EXAMPLE 6

In Vivo Assay

Blood Cyclosporin A Levels in Rats

Lewis cannulated rats (6 per group) were given either a single dose of 2.5 mg/kg cyclosporin A (Neoral Oral solution, Sandoz, East Hannover, N.J.) diluted in olive oil or a single dose of the same cyclosporin A followed by s.c. injections three times per day of 50 mg/kg of a non-peptide CCR1 receptor antagonist of the invention in 40% cyclodextrin. Whole blood was collected using EDTA as anticoagulant at various times post-dosing. Plasma cyclosporin A levels were measured using a Cyclo-Trac SP-Whole Blood Radioimmunoassay for Cyclosporin kit (DiaSorin, Stillwater, Minn.) basically following the manufacturer's instructions. A methanol extraction step was performed for the standards, controls and samples prior to assay. The methanol extracts were combined with $I^{125}$-labeled cyclosporin tracer. A mixture of a mouse monoclonal antibody specific for cyclosporin A and donkey anti-mouse antibody in a single reagent was added. Following a one hour incubation, the tubes were centrifuged, decanted, and counted. The amount of radioactivity in the pellet was inversely proportional to the concentration of cyclosporin A in the sample. A calibration curve was obtained using a 4-parameter logistic curve-fitting program by plotting the extent of binding against log concentration. Cyclosporin A concentrations were interpolated from the standard curve.

The non-peptide CCR1 receptor antagonists of the invention, when tested in this assay, did not significantly affect the elimination half-life of cyclosporin in the whole blood of rats.

EXAMPLE 7

In Vitro Assay: Monocyte Adhesion and Rolling

Functional in Vitro Assay for Non-Peptide CCR1 Receptor Antagonists

The interaction of monocytes with endothelium was studied in laminar flow assays essentially as described (Gröne, H. J. et al., (1999), supra, and Weber, K. S. et al., Eur. J. Immunol. (1999), Vol. 29, pp.700–712). Human dermal microvascular endothelial cells were grown to confluence in petri dishes and stimulated with 10 ng/ml IL-1β for 12 hours or left untreated. Prior to study the cells were pre-incubated with 10 ng/ml RANTES for 30 minutes. The plates were assembled as the lower wall in a parallel wall flow chamber and mounted on the stage of an Olympus IMT-2 inverted microscope with 20× and 40× phase contrast objectives. Human blood monocytes were isolated by Nycodenz hyperosmolaric gradient centrifugation and resuspended at $5 \times 10^6$ cells/ml in assay buffer (10 mM HEPES, 0.5% HSA, pH 7.4). Shortly before assay, the $Mg^{2+}$ and $Ca^{2+}$ concentrations were adjusted to 1 mM. The cell suspensions were kept in a heating block at 37° C. during the assay and perfused into the flow chamber at a rate of 1.5 dyn/cm² for 5 minutes. For inhibition experiments, monocytes were pre-incubated for 10 minutes at 37° C. with various concentrations of non-peptide CCR1 receptor antagonists of the invention or a DMSO control. The number of firmly adherent cells was counted in at least five fields by analysis of images recorded with a long integration JVC 3CCD video camera and a JVC SR 900 E video recorder. Results were expressed as cell/mm². As an inverse measure of adhesion, the number of monocytes rolling at low shear was assessed in the last 30 second interval of the five minute period and expressed as the percentage of the total interactions within the analyzed fields.

The non-peptide CCR1 receptor antagonists of the invention, when tested in this assay, inhibited the adhesion of monocytes to activated endothelial cells and increased the percentage of monocytes that undergo or maintain rolling.

EXAMPLE 8

This example illustrates the preparation of representative pharmaceutical compositions of the invention for oral administration:

| A. | Ingredients | % wt./wt. |
|---|---|---|
| | Active ingredients | 20.0% |
| | Lactose | 79.5% |
| | Magnesium stearate | 0.5% |

The above ingredients are mixed and dispensed into hard-shell gelatin capsules containing 100 mg each, one capsule would approximate a total daily dosage.

| B. | Ingredients | % wt./wt. |
|---|---|---|
| | Active ingredients | 20.0% |
| | Magnesium stearate | 0.9% |
| | Starch | 8.6% |
| | Lactose | 69.6% |
| | PVP (polyvinylpyrrolidine) | 0.9% |

The above ingredients with the exception of the magnesium stearate are combined and granulated using water as a granulating liquid. The formulation is then dried, mixed with the magnesium stearate and formed into tablets with an appropriate tableting machine.

| C. | Ingredients | |
|---|---|---|
| | Active ingredients | 0.1 g |
| | Propylene glycol | 20.0 g |
| | Polyethylene glycol 400 | 20.0 g |
| | Polysorbate 80 | 10 g |
| | Water | q.s. 100 mL |

The active ingredients are dissolved in propylene glycol, polyethylene glycol 400 and polysorbate 80. A sufficient quantity of water is then added with stirring to provide 100 mL of the solution, which is filtered and bottled.

| D. | Ingredients | % wt./wt. |
|---|---|---|
| | Active ingredients | 20.0% |
| | Peanut Oil | 78.0% |
| | Span 60 | 2.0% |

The above ingredients are melted, mixed and filled into soft elastic capsules.

| E. | Ingredients | % wt./wt |
|---|---|---|
| | Active ingredients | 1.0% |
| | Methyl or carboxymethyl cellulose | 2.0% |
| | 0.9% saline | q.s. 100 mL |

The active ingredients are dissolved in the cellulose/saline solution, filtered and bottled for use.

EXAMPLE 9

This example illustrates the preparation of a representative pharmaceutical composition of the invention for parenteral administration:

| Ingredients | |
|---|---|
| Active ingredients | 0.02 g |
| Propylene glycol | 20.0 g |
| Polyethylene glycol 400 | 20.0 g |
| Polysorbate 80 | 1.0 g |
| 0.9% Saline solution | q.s. 100 mL |

The active ingredients are dissolved in propylene glycol, polyethylene glycol 400 and polysorbate 80. A sufficient quantity of 0.9% saline solution is then added with stirring to provide 100 mL of the I.V. solution, which is filtered through a 0.2 μm membrane filter and packaged under sterile conditions.

EXAMPLE 10

This example illustrates the preparation of a representative pharmaceutical composition of the invention in suppository form:

| Ingredients | % wt./wt. |
|---|---|
| Active ingredients | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 11

This example illustrates the preparation of a representative pharmaceutical composition of the invention for insufflation:

| Ingredients | % wt./wt. |
|---|---|
| Micronized active ingredients | 1.0% |
| Micronized lactose | 99.0% |

The ingredients are milled, mixed, and packaged in an insufflator equipped with a dosing pump.

EXAMPLE 12

This example illustrates the preparation of a representative pharmaceutical composition of the invention in nebulized form:

| Ingredients | % wt./wt. |
|---|---|
| Active ingredients | 0.005% |
| Water | 89.995% |
| Ethanol | 10.000% |

The active ingredients are dissolved in ethanol and blended with water. The formulation is then packaged in a nebulizer equipped with a dosing pump.

EXAMPLE 13

This example illustrates the preparation of a representative pharmaceutical composition of the invention in aerosol form:

| Ingredients | % wt./wt. |
|---|---|
| Active ingredients | 0.10% |
| Propellant 11/12 | 98.90% |
| Oleic acid | 1.00% |

The active ingredients are dispersed in oleic acid and the propellants. The resulting mixture is then poured into an aerosol container fitted with a metering valve.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

I claim:

1. A pharmaceutical composition useful in treating heart transplant rejection in mammals, which composition comprises one or more pharmaceutically acceptable excipients, a therapeutically effective amount of a non-peptide CCR1 receptor antagonist and a sub-nephrotoxic amount of cyclosporin A.

2. The pharmaceutical composition of claim 1 wherein the non-peptide CCR1 receptor antagonist is a compound selected from formula (I):

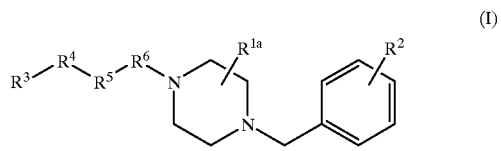

wherein:
   $R^{1a}$ is one or more substituents independently selected from the group consisting of alkyl or hydroxyalkyl;
   $R^2$ is fluoro at the 4-position;
   $R^3$ is phenyl substituted at the 4-position with chloro and at the 2-position by aminocarbonyl, ureido or glycinamido;
   $R^4$ is —O—;
   $R^5$ is methylene; and
   $R^6$ is —C(O)—;
as a single stereoisomer or a mixture thereof; or a pharmaceutically acceptable salt thereof.

3. The pharmaceutical composition of claim 2 wherein the non-peptide CCR1 receptor antagonist is selected from the group consisting of:
   (2R,5S)-1-((4-chloro-2-(aminocarbonyl)phenoxy)methyl)carbonyl-2,5-dimethyl-4-(4-fluorobenzyl)piperazine;
   (trans)-1-((4-chloro-2-(glycinamido)phenoxy)methyl)carbonyl-2,5-dimethyl-4-(4-fluorobenzyl)piperazine;

(2R)-1-((4-chloro-2-(ureido)phenoxy)methyl)carbonyl-2-methyl-4-(4-fluorobenzyl)piperazine;

(trans)-1-((4-chloro-2-(ureido)phenoxy)methyl)carbonyl-2,5-dimethyl-4-(4-fluorobenzyl)piperazine;

(2R,5S)-1-((4-chloro-2-(ureido)phenoxy)methyl)carbonyl-2,5-dimethyl-4-(4-fluorobenzyl)piperazine; and (2R,5S)-1-((4-chloro-2-(glycinamido)phenoxy)methyl)carbonyl-2,5-dimethyl-4-(4-fluorobenzyl)piperazine.

4. The pharmaceutical composition of claim 2 wherein the non-peptide CCR1 receptor antagonist is (2R)-1-((4-chloro-2-(ureido)phenoxy)methyl)carbonyl-2-methyl-4-(4-fluorobenzyl)piperazine.

5. The pharmaceutical composition of claim 4 wherein the mammal in need thereof is a human.

6. A method of administering to a mammal in need thereof a pharmaceutical composition useful in treating heart transplant rejection in mammals, wherein said method comprises administering said pharmaceutical composition to a mammal, which pharmaceutical composition comprises a one or more pharmaceutically acceptable excipients, a therapeutically effective amount at a non-peptide CCR1 receptor antagonist and a sub-nephrotoxic amount of cyclosporin A.

7. The method of claim 6 wherein the non-peptide CCR1 receptor antagonist and the cyclosporin A are administered to the mammal in need thereof simultaneously or sequentially.

8. The method of claim 7 wherein the non-peptide CCR1 receptor antagonist is a compound selected from formula (I):

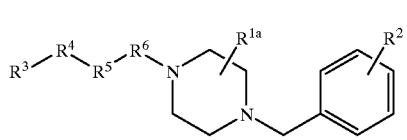

(I)

wherein:

$R^{1a}$ is one or more substituents independently selected from the group consisting of alkyl or hydroxyalkyl;

$R^2$ is fluoro at the 4-position;

$R^3$ is phenyl substituted at the 4-position with chloro and at the 2-position by aminocarbonyl, ureido or glycinamido;

$R^4$ is —O—;

$R^5$ is methylene; and $R^6$ is —C(O)—;

as a single stereoisomer or a mixture thereof; or a pharmaceutically acceptable salt thereof.

9. The method of claim 8 wherein the non-peptide CCR1 receptor antagonist is selected from the group consisting of:

(2R,5S)-1-((4-chloro-2-(aminocarbonyl)phenoxy)methyl)carbonyl-2,5-dimethyl-4-(4-fluorobenzyl)piperazine;

(trans)-1-((4-chloro-2-(glycinamido)phenoxy)methyl)carbonyl-2,5-dimethyl-4-(4-fluorobenzyl)piperazine;

(2R)-1-((4-chloro-2-(ureido)phenoxy)methyl)carbonyl-2-methyl-4-(4-fluorobenzyl)piperazine;

(trans)-1-((4-chloro-2-(ureido)phenoxy)methyl)carbonyl-2,5-dimethyl-4-(4-fluorobenzyl)piperazine;

(2R,5S)-1-((4-chloro-2-(ureido)phenoxy)methyl)carbonyl-2,5-dimethyl-4-(4-fluorobenzyl)piperazine; and (2R,5S)-1-((4-chloro-2-(glycinamido)phenoxy)methyl)carbonyl-2,5-dimethyl-4-(4-fluorobenzyl)piperazine.

10. The method of claim 8 wherein the non-peptide CCR1 receptor antagonist is (2R)-1-((4-chloro-2-(ureido)phenoxy)methyl)carbonyl-2-methyl-4-(4-fluorobenzyl)piperazine.

11. The method of claim 8 wherein the mammal in need thereof is a human.

12. A method of treating heart transplant rejection in a mammal, wherein said method comprises administering to a mammal in need thereof a pharmaceutical composition, said pharmaceutical composition comprising one or more pharmaceutically acceptable excipients, a therapeutically effective amount of a non-peptide CCR1 receptor antagonist and a sub-nephrotoxic amount of cyclosporin A.

13. The method of claim 12 wherein the non-peptide CCR1 receptor antagonist is a compound selected from formula (I):

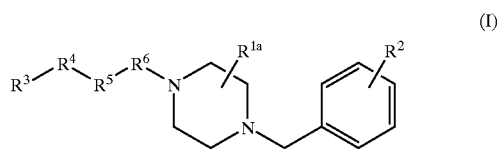

(I)

wherein:

$R^{1a}$ is one or move substituents independently selected from the group consisting of alkyl or hydroxyalkyl;

$R^2$ is fluoro at the 4-position;

$R^3$ is phenyl substituted at the 4-position with chloro and at the 2-position by aminocarbonyl, ureido or glycinamido;

$R^4$ is —O—;

$R^5$ is methylene; and $R^6$ is —C(O)—;

as a single stereoisomer or a mixture thereof; or a pharmaceutically acceptable salt thereof.

14. The method of claim 13 wherein the non-peptide CCR1 receptor antagonist is selected from the group consisting of:

(2R,5S)-1-((4-chloro-2-(aminocarbonyl)phenoxy)methyl)carbonyl-2,5-dimethyl-4-(4-fluorobenzyl)piperazine;

(trans)-1-((4-chloro-2-(glycinamido)phenoxy)methyl)carbonyl-2,5-dimethyl-4-(4-fluorobenzyl)piperazine;

(2R)-1-((4-chloro-2-(ureido)phenoxy)methyl)carbonyl-2-methyl-4-(4-fluorobenzyl)piperazine;

(trans)-1-((4-chloro-2-(ureido)phenoxy)methyl)carbonyl-2,5-dimethyl-4-(4-fluorobenzyl)piperazine;

(2R,5S)-1-((4-chloro-2-(ureido)phenoxy)methyl)carbonyl-2,5-dimethyl-4-(4-fluorobenzyl)piperazine; and (2R,5S)-1-((4-chloro-2-(glycinamido)phenoxy)methyl)carbonyl-2,5-dimethyl-4-(4-fluorobenzyl)piperazine.

15. The method of claim 13 wherein the non-peptide CCR1 receptor antagonist is (2R)-1-((4-chloro-2-(ureido)phenoxy)methyl)carbonyl-2-methyl-4-(4-fluorobenzyl)piperazine.

16. The method of claim 15 wherein the mammal in need thereof is a human.

17. The method of claim 15 wherein the non-peptide CCR1 receptor antagonist and the cyclosporin A are administered to the mammal in need thereof simultaneously or sequentially.

* * * * *